United States Patent [19]
Gerstel et al.

[11] Patent Number: 6,055,845
[45] Date of Patent: May 2, 2000

[54] METHOD FOR APPLYING SAMPLES TO BE ANALYZED BY GAS CHROMATOGRAPHY AND SAMPLING TUBE

[75] Inventors: Eberhard Gerstel; Ralf Bremer, both of Mulheim, Germany

[73] Assignee: Gerstel GmbH, Germany

[21] Appl. No.: 08/992,944

[22] Filed: Dec. 18, 1997

[30] Foreign Application Priority Data

Dec. 20, 1996 [DE] Germany .................. 196 53 406

[51] Int. Cl.⁷ .................. G01N 30/04; G01N 1/16; G01N 31/12; B01D 53/02
[52] U.S. Cl. .................. 73/23.42; 73/863.12; 96/105; 422/78
[58] Field of Search .................. 73/23.41, 23.42, 73/23.25, 863.11, 864.83, 863.21, 864.81, 23.35, 863.12; 96/105; 422/78

[56] References Cited

U.S. PATENT DOCUMENTS

| | | | |
|---|---|---|---|
| 3,964,872 | 6/1976 | Karinkanta | 73/864.82 |
| 4,344,917 | 8/1982 | Schorno | 422/78 |
| 4,849,179 | 7/1989 | Reinhardt et al. | 422/89 |
| 5,065,614 | 11/1991 | Hartman et al. | 73/23.35 |
| 5,434,665 | 7/1995 | Tobe et al. | 356/307 |
| 5,588,988 | 12/1996 | Gerstel | 96/101 |
| 5,672,810 | 9/1997 | Shibamoto | 73/23.25 |

Primary Examiner—Hezron Williams
Assistant Examiner—Jay L. Politzer
Attorney, Agent, or Firm—Douglas J. Christensen

[57] ABSTRACT

The invention relates to a method for applying samples to be analyzed by gas chromatography using a sampling tube, which has a section which contains the adsorbing agent and narrows essentially conically towards a bore which is free of adsorbing agent and has a reduced diameter, in such a manner that the flow rate of a gas which is guided through towards the narrowed section on the outlet side is at least approximately equal to the inlet-side flow rate, liquid or gaseous starting sample material being guided through the sampling tube towards the narrowed section, so that substances to be analyzed are adsorbed on the adsorbing agent, the sampling tube being flushed with drying gas, which is guided through the sampling tube in the same direction as the starting sample material, until the liquid phase, which is contained in the sampling tube, or the starting sample material is essentially removed, and the adsorbed sample being desorbed by means of a carrier gas which is introduced through the sampling tube from the narrowed side.

20 Claims, 3 Drawing Sheets

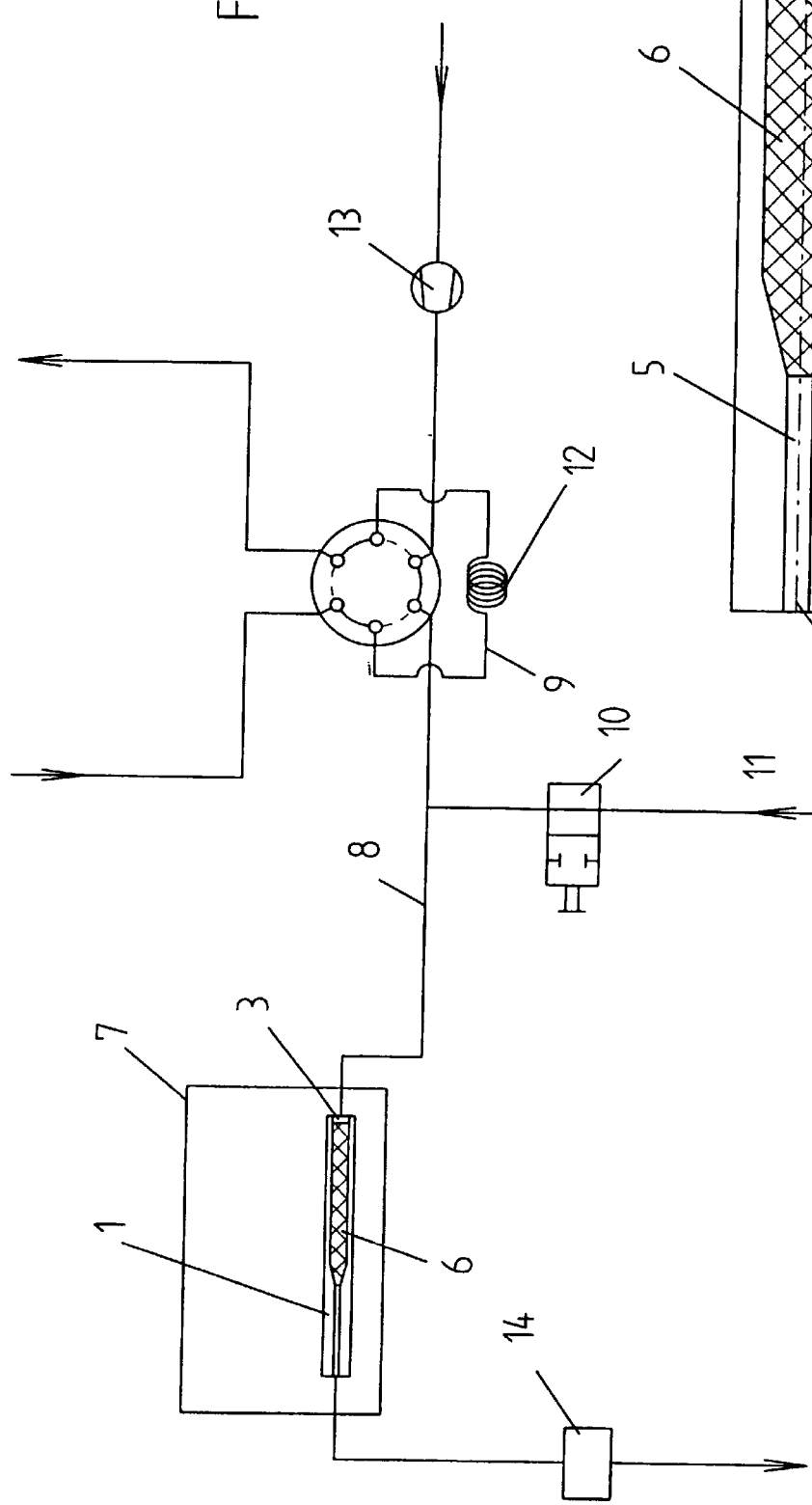

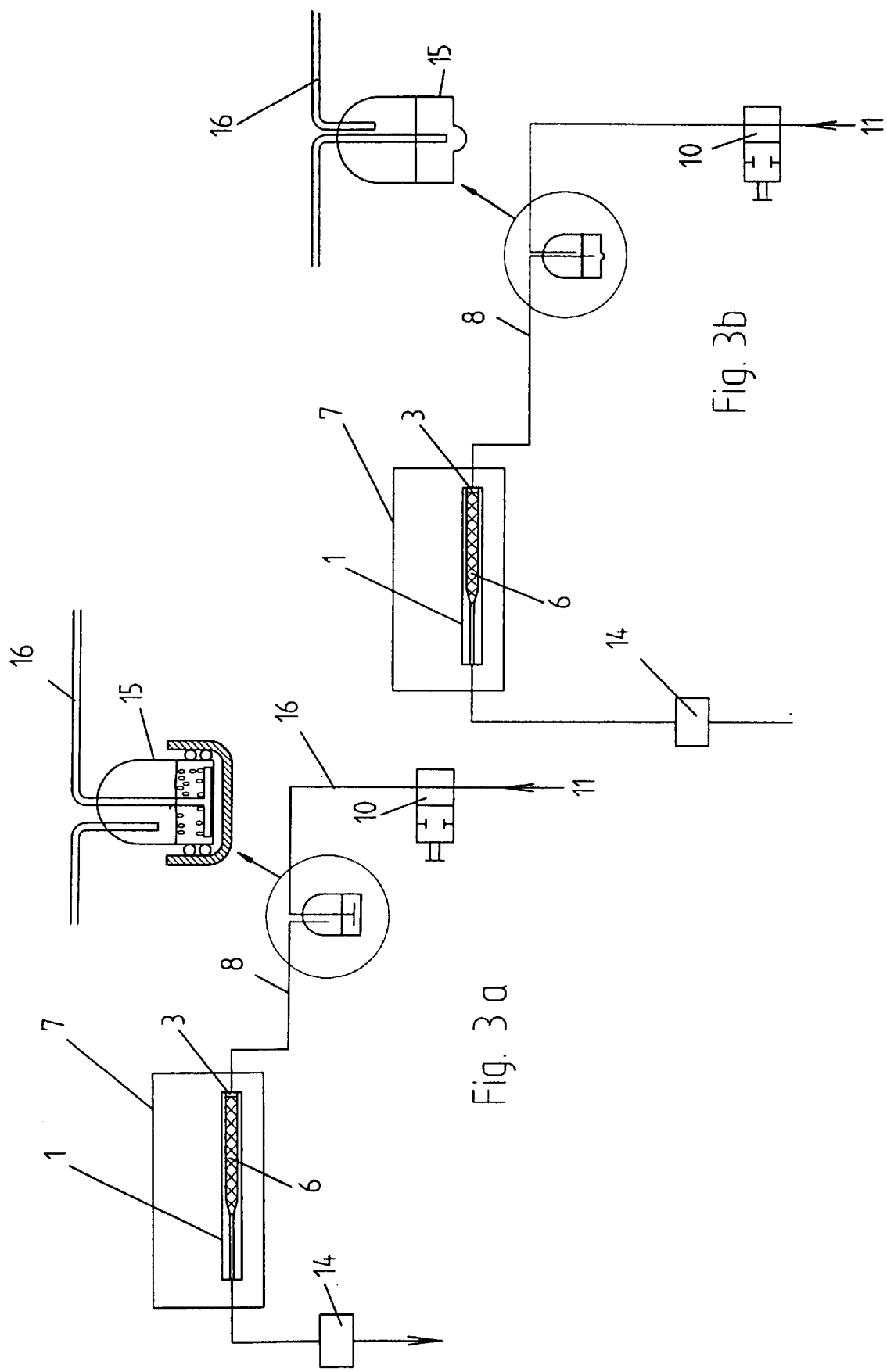

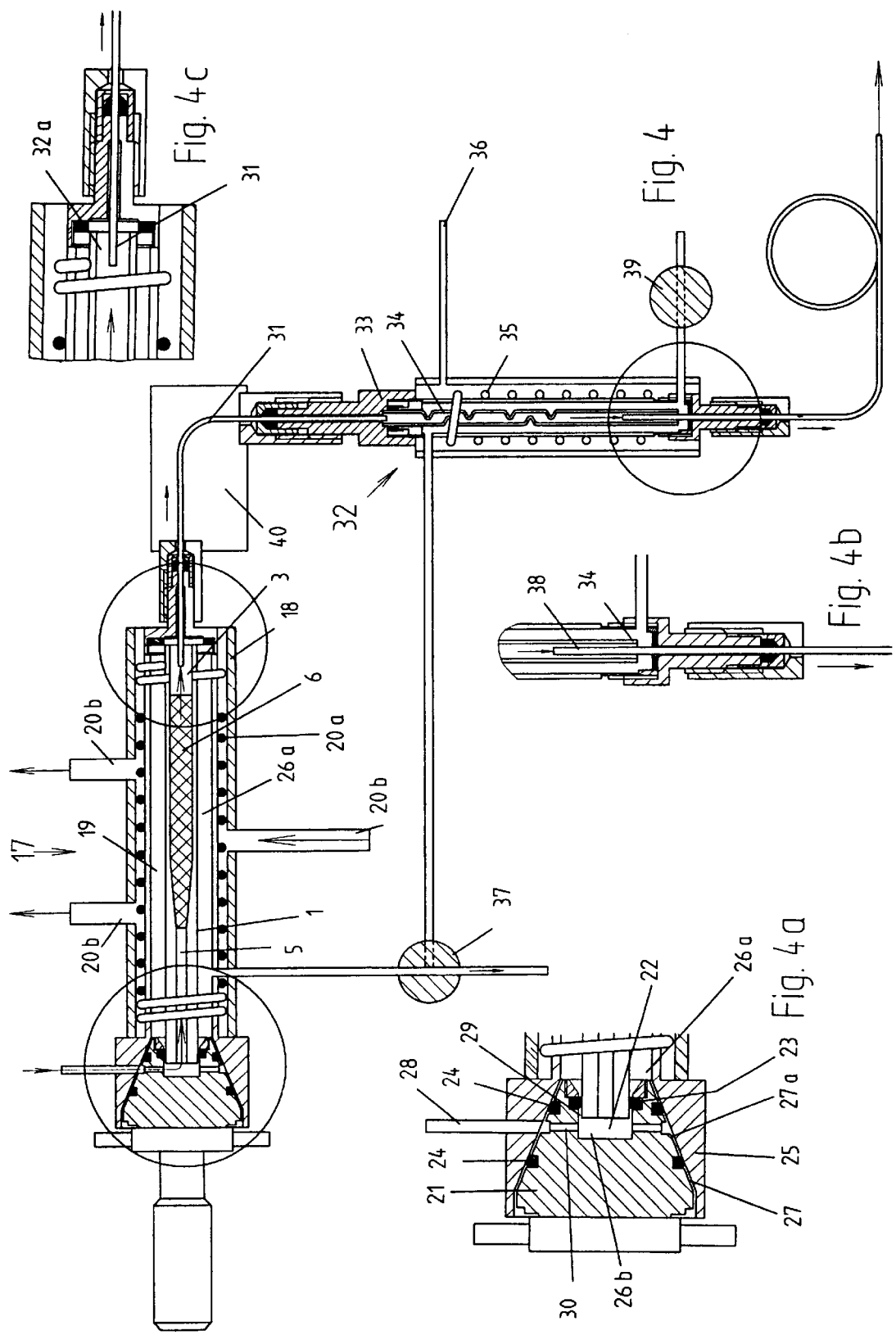

METHOD FOR APPLYING SAMPLES TO BE ANALYZED BY GAS CHROMATOGRAPHY AND SAMPLING TUBE

BACKGROUND OF THE INVENTION

The invention relates to a method and apparatus for analyzing samples by gas chromatography using a sampling tube.

German Patent DE 44 19 596 C1 has disclosed a thermal desorption device for a gas chromatograph with a temperature-controlled furnace which is provided with a carrier-gas connection and with an evaporator tube, the evaporator tube being an exchangeable sampling tube which can be received by a receiving chamber of the furnace and one end of which can be inserted into a receiving piece, sealed with respect to the outside by means of a seal, in which case the receiving piece has two seals, which are arranged spaced apart in the region of the casing, and can be inserted into a receptacle of corresponding design, the carrier-gas connection opening in the region of an annular gap between receptacle and receiving piece, between the two seals situated on the casing, which for its part is connected to an annular gap surrounding the inserted end of the sampling tube, with a trap connected downstream. In this case, the sampling tube may contain either a solid or volatile or semi-volatile substances adsorbed on an adsorbing agent as the sample. However, the sampling tube is not suitable for applying substances to be analyzed by gas chromatography which are contained in a liquid or liquid-vapor-laden gaseous starting sample material, since liquid contained in the starting sample material would freeze in the downstream trap and would block the gas chromatograph.

European patent application EP 0 245 642 A1 has likewise disclosed a method for sampling by means of thermal desorption using a sampling tube, in which method adsorbed substances are desorbed on a capillary column of a gas chromatograph by means of a carrier gas via an injector containing the sampling tube.

The object of the invention is to provide a method and sampling tube which make it possible to analyze substances originating from liquid or liquid-vapor-laden gaseous starting sample material with as little loss as possible and without freezing.

SUMMARY OF THE INVENTION

A sampling tube is used which has a section which contains the adsorbing agent and narrows essentially conically to a bore, which is free of adsorbing agent and has a reduced diameter, in such a manner that the flow rate of a gas which is guided through towards the narrowed section on the outlet side is at least approximately equal to the inlet-side flow rate. This makes it possible to adsorb on the adsorbing agent, from liquid or gaseous starting sample material, in particular in the form of an aqueous liquid or an essentially liquid-vapor-saturated gas phase, the substances of the sample in the sampling tube which are to be analyzed, by guiding the liquid or gaseous starting sample through the sampling tube towards the narrowed section, and to dry the adsorbed sample, by flushing with a drying gas, which is guided through the sampling tube in the same direction as the starting sample material, until the liquid phase, which is contained in the sampling tube, of the starting sample material is essentially removed. The sampling tube is then inserted into a thermal desorption device of a gas chromatograph and the adsorbed sample is desorbed by means of a carrier gas which is introduced through the sampling tube from the narrowed side.

As a result, it is possible to analyze in particular aqueous liquids, for example beer, wine, milk, drinking water, waste waters, ground water or the like, by gas chromatography in a simple manner and, for example with continuous sampling. However, this method can also be used to analyze substances contained in organic solvents.

There is virtually no occurrence of contamination which would be introduced in the event of desorption using solvent, since gases used for desorption can be kept very pure.

Further configurations of the invention are to be found in the following description.

BRIEF DESCRIPTION OF THE DRAWINGS

FIG. 1 shows an enlarged view of a sampling tube.

FIG. 2 diagrammatically shows a device for charging a sampling tube from FIG. 1.

FIGS. 3a and 3b diagrammatically show two further devices for charging a sampling tube from FIG. 1.

FIG. 4 shows a thermal desorption device for a sampling tube from FIG. 1.

FIG. 4a is an enlarged view of a portion of the thermal desorption device of FIG. 4.

FIG. 4b is an enlarged view of a portion of the thermal desorption device of FIG. 4.

DETAILED SPECIFICATION

The sampling tube 1 illustrated in FIG. 1 has a through-bore 2 with a region 3 which is open at one end, has a large diameter and narrows via an essentially conical section 4 towards a narrowed region 5 with a small diameter. The region 3 and the conical section 4 accommodate an adsorbing agent 6, which may optionally be situated on a carrier material. The diameters of the regions 3 and 5 are matched to one another in such a manner that the flow rate of a gas guided through towards the narrowed region 5 in this narrowed region is at least approximately equal to the flow rate in the widened region 3 which is for its part narrowed by the adsorbing agent. That is, the reduced open area through the adsorbing agent in the widened region substantially equals the area through the reduced diameter region. In this way, virtually all the liquid which is introduced during the charging of the sampling tube 1 can be flushed out using a drying gas, such as nitrogen or a noble gas (helium), without the formation of dead zones in which considerable quantities of liquid remain.

The sampling tube 1 expediently consist of glass, although other materials, such as stainless steel, may also be used, and expediently has a constant external diameter in order to allow simple, optionally automatic, handling.

In accordance with FIG. 2, a magazine 7 for sampling tubes 1 is provided, a sampling tube 1 being situated in the charging position. This sampling tube 1 is positioned in such a manner that the widened region 3 is situated on the inlet side and is connected to a line 8. The line 8 is connected, on the one hand, to a bypass injector 9 and, on the other hand, to a drying-gas source 11 via a valve 10.

The bypass injector 9 comprises a receiving tube 12 for starting sample material, which in the position shown in solid lines flows through the bypass injector 9 and its receiving tube 12. The receiving tube 12 is, for example, a stainless steel tube of predetermined length and predetermined diameter and hence of predetermined receiving volume, which is expediently wound up into a spiral.

After charging the receiving tube 1, the bypass injector 9 switches over into the position shown in dashed lines, in which a pump 13 forces a conveying liquid, for example distilled water, into the bypass injector 9, with the result that the starting sample material is forced out of the receiving tube 12 and is guided, via the line 8, through the sampling tube 1, where substances contained in the starting sample material are adsorbed on the adsorbing agent 6.

Using the bypass injector 9 permits a distortion-free application of the starting sample material, so that memory effects are avoided. With starting sample materials where there is no risk of such effects, the application may also be carried out directly, without the intervention of the bypass injector 9.

When the starting sample material has been guided through the sampling tube 1, the drying-gas source 11 is connected up via the valve 10 and guides drying gas through the sampling tube 1 in the same direction as the starting sample material until the sample taken from this material has practically been dried. This can be monitored by means of a thermal conductivity detector 14, which on a suitable output signal ends the supply of the drying gas.

In accordance with FIG. 3a, the sampling tube 1 may also be charged by connecting it to a line 8' which opens into a bottle-like sample vessel 15 above the liquid level of a liquid contained therein as starting sample material. Furthermore, a line 16 for extraction gas, such as nitrogen, air or the like, leads into the optionally heatable sample vessel 15, which line 16, below the liquid level, opens onto an open-pore body which forms gas bubbles. Rising gas bubbles are laden or saturated both with substances to be analyzed and with liquid vapor, so that liquid is also introduced into the sampling tube 1. This liquid is removed from the sampling tube 1 in the drying step.

In accordance with FIG. 3b, the line 16 may open out above the liquid level of the liquid situated in the sample vessel 15, while the line 8' reaches as far as the bottom of the sample vessel 15. As a result, the liquid situated in the sample vessel 15 can be forced out of the line 16, by the gas, directly into the sampling tube 1, in which case, after termination of the transfer of the liquid, the gas is used for drying. In order to leave as little liquid remaining in the sample vessel 15 as possible, the sample vessel 15, as indicated in FIG. 3b, may have a depression on the bottom side or may be of approximately conical design on the underside.

A suitable liquid is generally a solvent, in particular water, or a solvent mixture, e.g. water and alcohol, for the substances to be analyzed.

In accordance with FIG. 4, the charged sampling tube 1 is inserted into a thermal desorption device 17 of a gas chromatograph, as is essentially known from DE 44 19 569 C1, with the widened region 3 as the inward end, so that desorption is carried out counter to the charging direction. The thermal desorption device 17 comprises a furnace 18 which can be cooled and heated in a controlled manner and has an inner receiving chamber 19, which is surrounded, on the one hand, by a heating device 20a for the controlled heating of a receiving chamber 19 and, on the other hand, by coolant bores 20b, which are connected to a coolant source, for example a liquid-nitrogen source.

The receiving chamber 19 serves to receive in an exchangeable manner a sampling tube 1, for which a receiving piece 21 is provided, which has an axially central blind bore 22 which is provided, next to its opening, with a groove which accommodates an O-ring 23. The outside of the receiving piece 21 is of conical design and is provided with two grooves arranged spaced apart on its conical surface, each of which accommodates an O-ring 24. The blind bore 22 accommodates one end of the sampling tube 1 in an exchangeable manner.

At its end which is open towards the outside, the receiving chamber 19 has a frustoconical receptacle 25 for the receiving piece 21 and, with the sampling tube 1, forms an annular gap 26a. With the receiving piece 21 inserted, the O-rings 24 seal off a section 27a of an annular gap 27 between the receiving piece 21 and the receptacle 25, into which section a carrier-gas line 28 opens. That region of an annular gap 29, surrounding the sampling tube 1 in the blind bore 22, which is sealed with respect to the receiving chamber 19 by the O-ring 23 is connected via a bore 30 to the section 26b of the annular gap 29 and hence to the carrier-gas line 28, so that carrier gas supplied via the carrier-gas line 28 can flow into the sampling tube 1.

A transfer capillary 31, which leads to a trap 32, opens into the receiving chamber 19, inside the sampling tube 1. The transfer capillary 31 projects to some extent into the receiving chamber 19, so that when the sampling tube 1 is introduced it is to this extent accommodated by the latter, forming an annular gap 32a.

A suitable trap 32 is, for example, a sample application device as is described in EP 0 451 566 A1. This device comprises a head 33 with an evaporator tube 34 arranged therein, which evaporator tube can be cooled and heated in a controlled manner by means of a suitable cooling and heating device 35, 36. A temperature sensor (not shown) and a control device, which is not shown and if appropriate also regulates the controlled heating of the furnace 18 by means of a corresponding temperature sensor, is provided for this purpose.

The evaporator tube 34 may be unfilled and provided with vortexing inserts or may be filled with an adsorbing agent, such as glass wadding, or may be provided with an inner coating or filled with an application-dependent adsorbing agent.

A pneumatic, ventilated closure 39, which is connected to the carrier-gas source, is provided at the outlet end of the vaporator tube 34, into which a gas-chromatographic capillary 38 is introduced, forming an annular gap. When the closure 39 is opened, carrier gas flows past the capillary 38, through the evaporator tube 34 and the transfer capillary 31, into the sampling tube 1. The carrier gas flows further through the annular gap 19 and a discharge line with a correspondingly open changeover valve 37. The carrier gas flowing through the sampling tube 1 is thus prevented from penetrating into the trap 32. Rather, in this way liquid which may have been adsorbed on the adsorbing agent or on the substances adsorbed thereon can be desorbed and removed from the system. This second drying step may, if appropriate, be carried out at elevated temperature in order simultaneously to remove high-boiling substances.

The thermal desorption of the substances of the sample in the sampling in the sampling tube 1 which are to be analyzed takes place by guiding carrier gas through the sampling tube 1, from its end with the narrower region 5 to the wider region 3, the thermally desorbed substances being collected in the trap 32. The thermal desorption device 17 in this case operates with split (changeover valve 37 in the position illustrated), while the trap 32 is without split. The substances are then applied to the capillary 38, the trap 32 operating with or without split.

The transfer capillary 31 is arranged in a transfer chamber 40, which controls the temperature of the capillary and extends from the furnace 18 to the head 33, in order to avoid losses of substance as a result of condensation.

The carrier gas may also serve as a flushing gas between the individual thermal desorptions.

Depending on the concentration of the substances to be analyzed, it is possible to operate the thermal desorption device 17 and also the trap 32 with or without split.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

We claim:

1. Method for applying samples to be analyzed by gas chromatography using a sampling tube, the substances to be analyzed of the sample being adsorbed by an adsorbing agent arranged in the sampling tube and the sampling tube being inserted into a thermal desorption device of a gas chromatograph for desorbing the substances to be analyzed, the method comprising the steps of:

a) utilizing a sampling tube which has an inlet side with a first section which contains the adsorbing agent extending across the cross-section of said first section, the sampling tube narrows essentially conically to an outlet side with a narrowed second section with a bore which has a reduced diameter and is free of the adsorbing agent and has a reduced diameter, the sampling tube configured such that when a gas is guided from the inlet side towards the outlet side, the flow velocity of the gas at the narrowed second section on the outlet side is substantially the same or greater than the velocity of the gas at the first section;

b) guiding a liquid or gaseous starting sample material, in particular in the form of an aqueous liquid or an essentially liquid-vapor-saturated gas phase, through the sampling tube from the inlet side towards the narrowed second section, so that substances to be analyzed are adsorbed on the adsorbing agent;

c) flushing the sampling tube with drying gas through the sampling tube in the same direction as the starting sample material, until the liquid phase, which is contained in the sampling tube, or the starting sample material is substantially removed; and d) introducing through the sampling tube from the outlet side a carrier gas whereby the adsorbed sample is desorbed.

2. Method according to claim 1, further comprising monitoring the drying by a thermal conductivity detector.

3. The method according to claim 1, further comprising a further drying of the sample in the thermal desorption device by means of a carrier gas prior to the desorption.

4. The method according to claim 3, wherein the further drying is performed at an elevated temperature.

5. The method according to claim 3, further comprising pneumatically closing a trap of the thermal desorption device during the further drying.

6. The method as in claim 1, wherein the starting sample material is initially taken up by a bypass injector and is then guided through the sampling tube.

7. The method as in claim 1, wherein the starting sample material is transferred into the sampling tube from a sample vessel by means of gas.

8. The method of claim 5 wherein the starting sample material is initially taken up by a bypass injector and is then guided through the sampling tube.

9. The method of claim 5 wherein the starting sample material is transferred into the sampling tube from a sample vessel by means of gas.

10. A method for applying samples to be analyzed by a gas chromatograph with a thermal desorption device capable of receiving a sampling tube, the method comprising the steps of:

a) utilizing a sampling tube which has an inlet side with a first section which contains the adsorbing agent and narrows essentially conically to an outlet side with a narrowed second section with a bore which has a reduced diameter and is free of the adsorbing agent and has a reduced diameter, the sampling tube configured such that when a gas is guided from the inlet side towards the outlet side, the velocity of the gas at the narrowed second section on the outlet side is at least approximately equal to the velocity of the gas at the first section;

b) guiding a liquid or gaseous starting sample material through the sampling tube from the inlet section towards the narrowed section, so that substances to be analyzed are adsorbed on the adsorbing agent;

c) flushing the sampling tube with drying gas through the sampling tube in the same direction as the starting sample material, until the liquid phase, which is contained in the sampling tube, is essentially removed;

d) inserting the sampling tube into the thermal desorption device; and e) introducing through the sampling tube from the outlet side a carrier gas whereby the adsorbed sample is desorbed by thermal desorption.

11. Method according to claim 10, further comprising monitoring the drying by a thermal conductivity detector.

12. The method according to claim 10, further comprising a further drying of the sample in the thermal desorption device by means of a carrier gas prior to the desorption.

13. The method according to claim 12, wherein the further drying is performed at an elevated temperature.

14. The method of claim 12, further comprising pneumatically closing a trap of the thermal desorption device during the further drying.

15. The method as in claim 10, wherein the starting sample material is initially taken up by a bypass injector and is then guided through the sampling tube.

16. The method as in claim 10, wherein the starting sample material is transferred into the sampling tube from a sample vessel by means of gas.

17. The method of claim 14, wherein the starting sample material is initially taken up by a bypass injector and is then guided through the sampling tube.

18. The method of claim 14 wherein the starting sample material is transferred into the sampling tube from a sample vessel by means of gas.

19. The methodology of claim 10 wherein the starting sample material is in the form of an aqueous liquid.

20. The methodology of claim 10 wherein the starting sample material is in the form of an essentially liquid-vapor-saturated gas phase.

* * * * *